United States Patent [19]
Heiple

[11] Patent Number: 4,696,292
[45] Date of Patent: Sep. 29, 1987

[54] TOOL FOR USE IN ANCHORING IMPLANTABLE PROSTHESIS AND METHOD

[76] Inventor: Kingsbury G. Heiple, 2410 Derbyshire Rd., Cleveland Heights, Ohio 44106

[21] Appl. No.: 751,327

[22] Filed: Jul. 2, 1985

[51] Int. Cl.$^4$ .............................................. A61F 5/04
[52] U.S. Cl. .......................... 128/92 V; 128/92 VP; 128/92 VJ
[58] Field of Search .......... 128/92 X, 92 XL, 92 XP, 128/303 R, 317, 305.1, 310, 92 V, 92 VL, 92 VP, 92 VJ

[56] References Cited

U.S. PATENT DOCUMENTS

| | | | |
|---|---|---|---|
| 1,322,644 | 11/1919 | Steiner | 128/317 |
| 1,377,288 | 5/1921 | Soresi | 128/317 |
| 1,630,239 | 5/1927 | Binkley et al. | 128/305.1 |
| 1,770,240 | 7/1930 | Magnuson | 128/317 |
| 2,287,260 | 6/1942 | Luck | 128/317 |
| 2,712,823 | 7/1955 | Kurtin | 128/303 R |
| 3,472,229 | 10/1969 | Kuntscher | 128/317 |
| 3,894,339 | 7/1975 | Manzi | 433/166 |
| 4,399,813 | 8/1983 | Barber | 128/92 EC |

OTHER PUBLICATIONS

*Machinery's Handbook*, 20th ed., "Milling Cutters," pp. 1606+.

Primary Examiner—C. Fred Rosenbaum
Assistant Examiner—C. W. Shedd
Attorney, Agent, or Firm—Baldwin, Egan, Hudak & Fetzer

[57] ABSTRACT

A cutting tool for preparing a femur for the receipt of an implantable prosthesis comprising a rotatable drive member adapted for removable coupling to a motor unit of a power assembly, with the tool being adapted to be received interiorly of the intramedullary canal of the femur and including a cylindrical-like cutter secured to the drive member for cutting into a confronting interior surface of the femur canal, together with shoulders on both sides of the cutter for limiting the depth of groove produced by the cutter upon rotation of the tool and movement of the cutter laterally into engagement with the canal surface. The canal is adapted to receive surgical cement in which the prosthesis is embedded, and with the cement entering the formed grooves in the interior surface of the canal for aiding in firmly anchoring the prosthesis in the canal upon hardening of the cement. A novel method for preparing the femur for the receipt of an implantable prosthesis by forming grooves therein is also disclosed.

9 Claims, 7 Drawing Figures

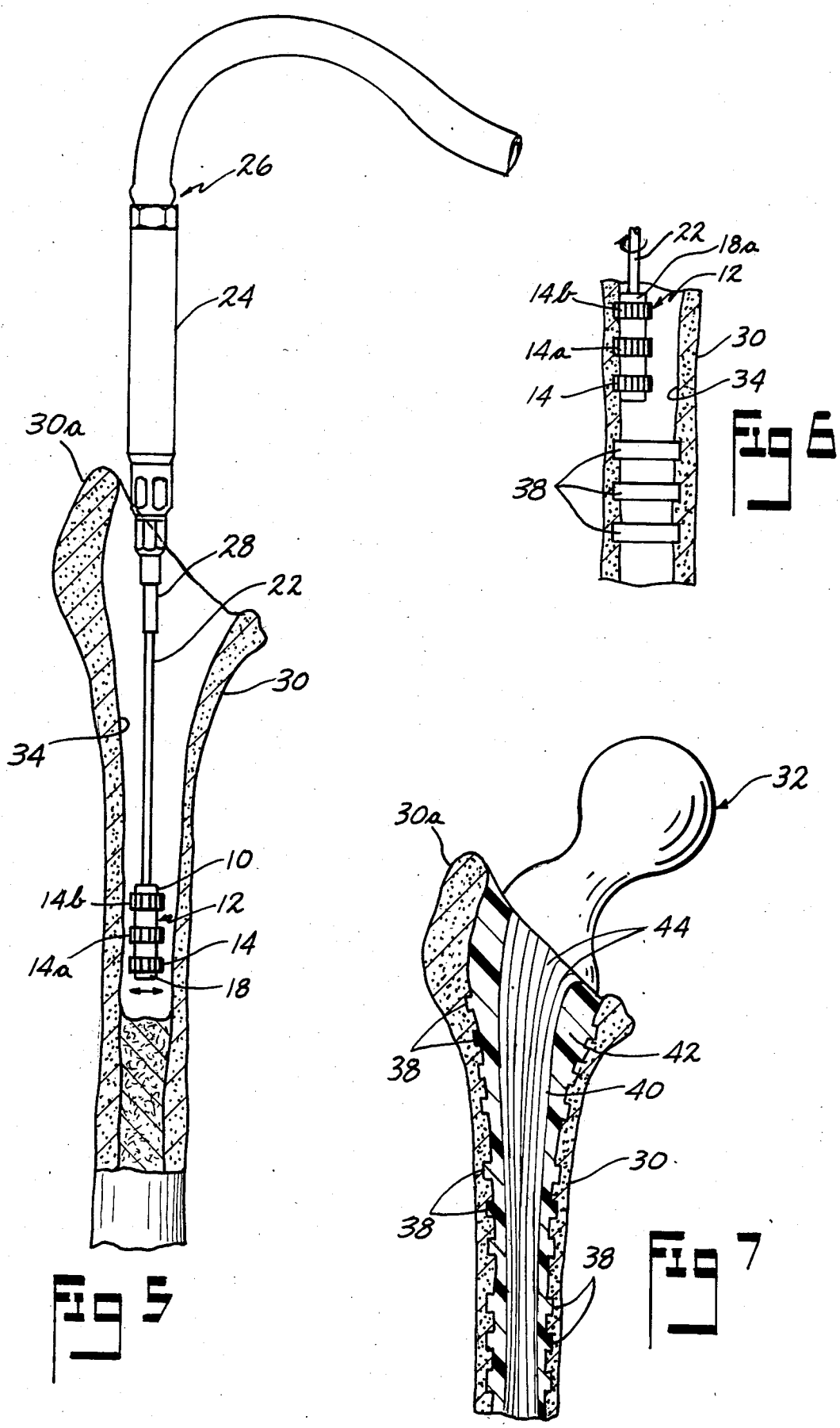

TOOL FOR USE IN ANCHORING IMPLANTABLE PROSTHESIS AND METHOD

The present invention relates to a tool for use in preparing a femur for the receipt of an implantable prosthesis by forming grooves in the interior surface of the intramedullary canal of the femur, with the grooves being adapted to receive therein surgical cement which upon hardening firmly anchors the implanted prosthesis in the canal. The tool includes a rotatable cutter section for forming the grooves in the femur interior surface, together with shoulders for limiting the depth of groove cut into the interior surface by the tool.

BACKGROUND OF THE INVENTION

It is well known in the art to implant a prosthesis in the intramedullary canal of a femur in connection with hip replacement of a human. Surgical cement is conventionally used for anchoring the prosthesis in the canal. Sometimes the prosthesis loosens in the cement, resulting in the necessity for the patient to re-undergo surgery to re-cement the prosthesis in place.

Rotatable cutter tools adapted to be driven by some form of motor unit are known in the hip replacement art as well as in many other areas of the medical arts.

U.S. Pat. No. 4,399,813 dated Aug. 23, 1983 in the name of Forest C. Barber and entitled Apparatus and Method for Removing a Prosthesis Embedded in Skeletal Bone, discloses a rotatable cutter or burr for forming an undercut ledge in a fragment of a prosthesis, for aiding in removal of the prosthesis fragment from embedment in a bone. Such rotatable cutter or burr does not embody any means for limiting or defining a predetermined amount of undercutting resulting from operation of the tool nor is there any teaching of a method in such patent relating to preparation of a human femur for receipt of an implantable prosthesis by providing grooves in the interior surface of the intramedullary canal of the femur.

Various other patents are known in the art which disclose tools for use in hip replacement; however, none of these patents to applicant's knowledge, teach a method of preparing a femur for an implantable prosthesis by providing grooves in the interior surface of the intramedullary canal of the femur, nor tools especially adapted for use in creating grooves in the intramedullary canal of the femur.

SUMMARY OF THE INVENTION

The present invention provides a novel tool for use in preparing a human femur for the receipt of an implantable prosthesis by providing for the cutting of grooves in the interior surface of the intramedullary canal of the femur, so that the surgical cement utilized for cementing the prosthesis in the canal enters the prepared grooves and more firmly anchors the prosthesis in the canal upon hardening of the cement. The invention also provides a novel method for preparing the femur for the receipt of an implantable prosthesis by providing for the cutting of grooves in the interior surface of the femoral canal.

Accordingly, an object of the invention is to provide a novel tool and method for preparing a human femur for the receipt of an implantable prosthesis.

A still further object of the invention is to provide a tool of the aforementioned type which includes means thereon for limiting the depth of groove or grooves able to be cut into the interior surface of the femoral canal.

A still further object of the invention is to provide a tool of the aforementioned type which includes a plurality of cutters on the rotatable tool spaced lengthwise thereof, for simultaneously cutting spaced grooves in the confronting surface of the canal of the femur.

A still further object of the invention is to provide a novel method for preparing a femur for the receipt of an implantable prosthesis by moving a rotatable cutter tool laterally into engagement with the confronting interior surface of the femoral canal to cut grooves in the interior surface thereof, and which are subsequently adapted to receive surgical cement therein which upon hardening more firmly anchors the prosthesis in the canal.

Other objects and advantages of the invention will be apparent from the following description taken in conjunction with the accompanying drawings wherein:

BRIEF DESCRIPTION OF DRAWINGS

FIG. 5 is a partially sectioned elevational view of a human femur that has had the head portion thereof severed in preparation for receiving an implantable prosthesis, and illustrating a tool embodying the invention inserted in the intramedullary canal of the femur preparatory to providing grooves in the confronting surface of the femoral canal;

FIG. 6 is a fragmentary sectional view illustrating the tool shown in FIG. 5 having been moved laterally into engagement with the confronting surface of the femoral canal to provide a plurality of grooves therein spaced lengthwise of the femoral canal; and FIG. 7 is a fragmentary sectional view of the human femur showing the prosthesis implanted in the intramedullary canal of the femur and with the surgical cement having entered the formed grooves in the defining interior surface of the femoral canal for aiding in anchoring the prosthesis upon hardening of the cement.

DESCRIPTION OF PREFERRED EMBODIMENT AND ALTERNATE EMBODIMENTS

Figure 1:
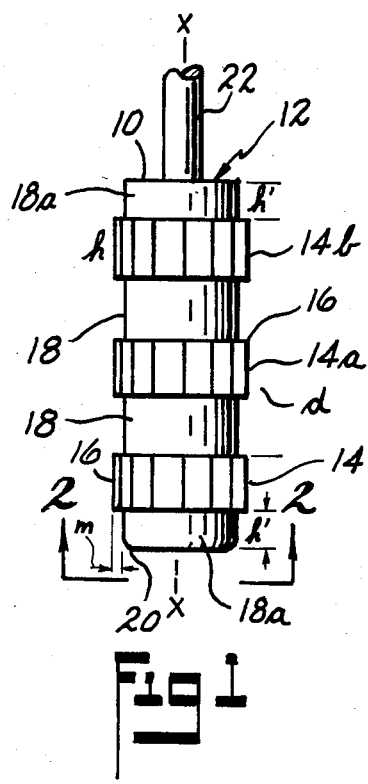
FIG. 1 is a fragmentary, side elevational view of a rotatable tool embodying the invention.
Figure 2:
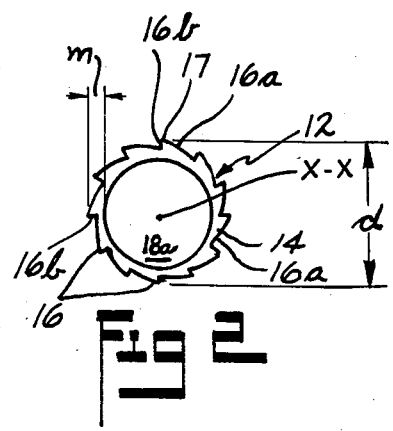
FIG. 2 is a end plan view of the tool of FIG. 1 taken generally along the plane of line 2—2 of FIG. 1 looking in the direction of the arrows.

Referring now again to FIG. 1, there is shown the head portion 10 of a rotatable cutter tool 12 embodying the invention, with the head portion of the tool in this embodiment comprising three cutter sections 14, 14a, 14b spaced relative to one another lengthwise of the tool. Each cutter section 14, 14a, 14b comprises a disc-like cutter or burr including peripheral cutter teeth 16 (FIG. 2), each of which preferably has a convex-like exterior periphery or heel portion 16a terminating at a point 17 disposed in the planar frontal surface 16b of the respective tooth, which in turn is disposed in a plane passing generally through the lengthwise axis X—X (FIG. 1) of the tool 12.

In accordance with the invention, means are provided on both sides of each of said cutter sections 14, 14a and 14b, for limiting the depth of groove able to be produced by the tool upon rotation thereof and cutting engagement thereof with a surface to be grooved. Such means in the embodiment illustrated, comprises shoulders in the form of cylindrical-like sections 18, 18a. Shoulder 18a on the distal end of the tool 12 is rounded off as at 20, for a purpose to be hereinafter described.

Stem portion 22 extends upwardly from the proximal end of head portion 10 and is adapted for connection to a powered motor unit 24 (FIG. 5) of medical pneumatic power assembly 26. Motor 24 may be a pneumatic motor of known type and which includes a chuck 28 adapted to receive therein the drive member or stem 22 of the tool 12, for causing rotation of the cutter head about its lengthwise axis upon actuation of power assembly 26.

Medical power assemblies of the type indicated are available from various manufacturers, such as, for instance, The Anspach Effort, Inc. company of Lake Park, Fla. While a pneumatically driven power assembly has been referred to, it will be understood that the power assembly per se forms no inventive part of the present arrangement and such power assembly could be, for instance, an electrically driven power assembly, rather than a pneumatic power assembly.

Referring now again to FIG. 5, there is illustrated a human femur 30 wherein the portion of the femur head 30a which forms the ball part of the hip joint has been removed for replacement by an implantable prosthesis which is the femoral component 32 illustrated in FIG. 7. The intramedullary canal 34 of the femur 30 has had the conventional marrow cleared therefrom for a predetermined extent of the length thereof, preparatory to receiving the implanted femoral component 32.

The tool 12 attached to the power assembly 26 is inserted into the intramedullary canal as shown, and the motor 24 of the power assembly is actuated to cause rotation of the tool 12, and then the rotating cutter head of the tool is moved laterally into engagement with the interior surface of the femoral canal, thus cutting grooves (and in the embodiment illustrated three spaced grooves 38) in the interior surface. Preferably the grooves are extended circumferentially around the entire defining periphery of the canal, and as illustrated for instance, in FIG. 6, by moving the tool in a generally circular motion about the defining periphery of the canal during the groove cutting operation.

The teeth of the cutter sections 14, 14a and 14b cut into the interior surface of the canal and are positively limited in the permissible lateral movement of the tool relative to the canal, and thus limiting the depth of the produced grooves, by the shoulders 18, 18a on the tool, which upon engagement with the interior surface of the canal prevent any further depth of cutting of the grooves.

Thus, it will be seen that even though the surgeon may not be able to see interiorly of the canal during preparation of the femur and use of the tool interiorly of the femur, such shoulders 18, 18a automatically limit the depth of groove able to be produced by the cutter sections.

After the desired number of grooves are produced in the canal utilizing the tool, with the grooves being spaced lengthwise of the femur canal as shown, for instance, in FIG. 7, the implantable prosthesis with its stem portion 40 is inserted into the canal along with the conventional surgical cement 42, for anchoring the prosthesis in the canal upon hardening of the cement.

The cement enters the produced grooves 38 in the canal and upon hardening, firmly anchors the prosthesis in the canal to help to prevent loosening thereof. In this connection, the stem 40 of the prosthesis may also be ribbed or grooved as at 44, to aid in anchoring the prosthesis in proper position in the canal, and to aid in preventing loosening thereof.

The following is an example of permissible and preferred dimensions of the cutter head sections and associated cutter teeth of the tool 12, in order to provide an indication of the depth of groove that is produced by the tool of the invention. Each of the cutter sections 14, 14a and 14b may have a height h or length with reference to the lengthwise extent of the tool of approximately 0.1875 inch, with the exterior diameter d of each cutter being of the order of 0.4375 inch, and with the limiting shoulders 18, 18a providing for a depth m (FIG. 2) of cutting in formation of the grooves 38 of approximately 1/32 inch. The distance between the cutter sections 14, 14a and 14b may be in the order of 0.1875 inch, with the end shoulders 18a being preferably of a lesser height h' (or length with respect to the lengthwise extent of the tool) as compared to the height of the shoulder portions 18. The maximum permissible depth of groove 38 is in the range of 1 to 3 millimeters. Rounding of the distal shoulder 18a as at 20 aids in manipulating the tool within the femoral canal.

Figure 3:
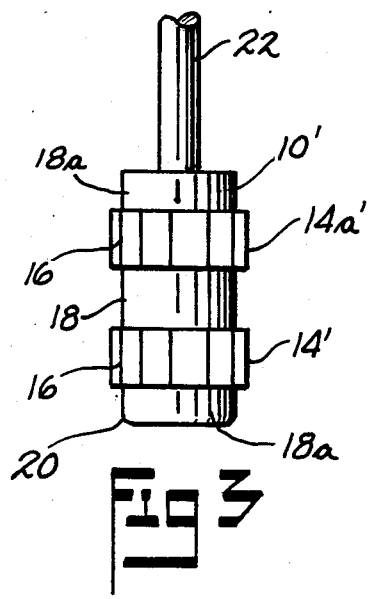
FIG. 3 is a fragmentary elevational view of a tool embodying the invention and showing a modified form of tool.

Referring now to FIG. 3, there is shown a modification of the tool of the invention, which instead of having three cutter sections only has two cutter sections 14' and 14a'. In other respects, the FIG. 3 tool head 10' may be generally similar to that of the FIGS. 1 and 2 tool.

Figure 4:
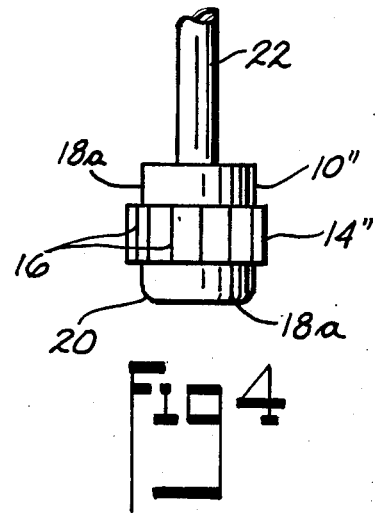
FIG. 4 is a fragmentary elevational view of a tool embodying the invention and showing a further modified form of tool.

FIG. 4 shows a further embodiment of tool head 10" which only has one cutter section 14" associated therewith, thus being able to produce only one groove in the intramedullary canal of the femur. In other respects, the FIG. 4 embodiment of rotary cutter tool 12" may be generally similar to those of the FIGS. 1 and 3 embodiments.

From the foregoing description and accompanying drawings, it will be seen that the invention provides a novel cutting tool and method for preparing a femur for the receipt of an implantable prosthesis, with the tool comprising a rotatable cutter head member which is adapted for removable coupling to a motor unit of a power assembly, with the tool being adapted to be received interiorly of the intramedullary canal of the femur, and which tool includes a cutter section or burr for cutting into a confronting interior surface of the femoral canal, together with shoulder means on both sides of the cutter for limiting the depth of groove able to be produced by the cutter upon rotation of the tool and movement of the cutter laterally into engagement with the canal surface, with the surgical cement utilized for cementing the prosthesis in the canal, entering the formed grooves in the interior surface of the canal, for aiding in firmly anchoring the prosthesis in the canal upon hardening of the cement.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

I claim:

1. In a method for preparing a femur for the receipt of an implantable prosthesis comprising clearing the medullary canal of marrow, inserting a cutting tool having a rotatable cutter thereon interiorly of said canal, rotating said cutter and moving said tool laterally in said canal into engagement with a confronting interior surface of the canal to cut a groove in said interior surface, withdrawing said tool from said canal and inserting surgical cement into said canal with a prosthesis, to implant said prosthesis in the cement in said canal, with said cement entering said groove for firmly anchoring said prosthesis in said canal upon hardening of said cement.

2. A method in accordance with claim 1 including the step of cutting a plurality of grooves in said interior surface in spaced relation lengthwise of said canal.

3. A method in accordance with claim 2 wherein at least certain of said plurality of grooves are simultaneously cut in said interior surface, and cutting each of said grooves to a depth within the range of approximately 1-3 millimeters.

4. A method in accordance with claim 1 including cutting said groove continuously circumferentially in said canal.

5. A method in accordance with claim 1 including the step of simultaneously cutting a plurality of grooves in said interior surface in spaced relation lengthwise of said canal.

6. A method in accordance with claim 1 including sequentially cutting a plurality of grooves in said interior surface in spaced relation lengthwise of said canal.

7. A method in accordance with claim 1 wherein said tool has a plurality of vertically spaced rotatable cutters thereon and including simultaneously rotating said cutters whereby a plurality of said grooves are cut into said interior surface in spaced relation lengthwise of said canal upon said lateral movement of said tool.

8. A method in accordance with claim 1 including limiting the lateral movement of said tool into cutting relationship with said interior surface by engaging said interior surface adjacent said cutter with a limiting shoulder on said tool, to thus limit the depth of the groove cut into said interior surface by said tool.

9. A method in accordance with claim 1 wherein said groove is cut into said interior surface for a depth within the range of approximately 1-3 millimeters.

* * * * *